United States Patent [19]

Umeda

[11] Patent Number: 4,834,069
[45] Date of Patent: May 30, 1989

[54] ENDOSCOPE WITH IMPROVED INSERTING PORTION

[75] Inventor: Hiroyuki Umeda, Kasukabe, Japan

[73] Assignee: Kabushiki Kaisha Machida Seisakusho, Tokyo, Japan

[21] Appl. No.: 231,456

[22] Filed: Aug. 12, 1988

[30] Foreign Application Priority Data

Sep. 3, 1987 [JP] Japan ............................ 62-133912[U]

[51] Int. Cl.$^4$ ............................................... A61B 1/00
[52] U.S. Cl. ......................................... 128/4; 138/120
[58] Field of Search ......................... 128/4, 6; 138/120

[56] References Cited

U.S. PATENT DOCUMENTS 1,905,824  4/1933  Dysthe ................................. 138/120
4,108,211  8/1978  Tanaka ................................ 138/120

Primary Examiner—William H. Grieb
Attorney, Agent, or Firm—Wegner & Bretschneider

[57] ABSTRACT

An endoscope comprising an operating body and an inserting portion extending therefrom. The inserting portion is provide with a bendable section which is composed of a plurality of tubular members arranged in facing relation to each other along an axis of the inserting portion. Each pair of adjacent tubular member are pivotally connected to each other. At least one pair of manipulating wires extend through the inserting portion to pivotally move each pair of adjacent tubular members relatively to each other, in order to curve the bendable section. A pair of wire guide members are fixedly received respectively in a pair of recesses formed in an inner peripheral surface of each tubular member. The manipulating wires extend respectively through the wire guide members on each tubular member.

8 Claims, 2 Drawing Sheets

ENDOSCOPE WITH IMPROVED INSERTING PORTION

BACKGROUND OF THE INVENTION

The present invention relates generally to endoscopes for use in observation of a body cavity in a human body, an interior of a machine and the like, and more particularly, to an improved inserting portion of the endoscope.

In general, an endoscope for observing a body cavity or a coelom in a human body comprises an operating body. The operating body is provided therein with an insertion opening for a forceps. An eyepiece barrel and one or more manipulating dials are mounted to the operating body. An inserting portion extends from the operating body, and is composed of a flexible section and a bendable section capable of being curved in at least one plane. A tip component is provided at a forward end of the bendable section remote from the operating body. The tip component is formed therein with a viewing window which is optically connected to the eyepiece barrel by an image-transmitting system. The tip component is further provided therein with a forceps opening which communicates with the forceps insertion opening in the operating body through a forceps channel. At least one pair of manipulating wires have their respective one ends fixedly connected to a shaft section of the manipulating dial which extends into the operating body. The manipulating wires extend through the inserting portion, and the other ends of the respective manipulating wires are fixedly connected to the tip component.

In use of the endoscope constructed as above, the inserting portion together with the tip component is inserted into, for example, the body cavity to be viewed. The manipulating dial is angularly moved about its axis to pull one of the pair of manipulating wires and to loosen the other manipulating wire. This causes the bendable section to be curved, thereby enabling the tip component to be oriented to a desirable direction. Thus, an observer can view any desirable part within the body cavity.

Various bendable sections for inserting portions of endoscopes of the kind referred to above are known from, for example, Japanese Utility Model Application Laid-Open Nos. 55-11250, 57-157302 and 60-190301. The known bendable section is composed of a plurality of tubular members arranged in coaxial relation to each other. Each pair of adjacent tubular members are pivotally connected to each other. At least one pair of tubular wire guides are mounted to an inner peripheral surface of each of the tubular members such that the pair of manipulating wires extend respectively through the pair of wire guides. When one of the pair of manipulating wires is pulled and the other manipulating wire is loosened in the manner described above, each pair of adjacent tubular members are pivotally moved relatively to each other so that the bendable section is curved as a whole.

It is difficult for the conventional bendable section, however, to fix each pair of wire guides to their respective positions on a corresponding one of the tubular members in a correct and accurate manner. By this reason, there may be a case where the wire guides mounted to one of each pair of adjacent tubular members are out of axial alignment with the respective wire guides on the other tubular member. Such misalignment causes an increase in frictional resistance between the manipulating wires and the inner peripheral surfaces of the respective wire guides when the manipulating wires are operated by the manipulating dial. The increase in frictional resistance deteriorates the operability of the manipulating dial, or causes tearing-up of the manipulating wires.

Another bendable sections are also known from Japanese Utility Model Publication Nos. 57-8801 and 58-46801, and Japanese Utility Model Application Laid-Open No. 60-187702. In the known bendable section, each pair of adjacent tubular members are pivotally connected to each other through a pair of pivots. Each pivot has an end portion thereof which projects radially inwardly from the inner peripheral surface of the tubular member. The projecting end portion of the pivot is formed therein with a guide bore. The pair of manipulating wires extend respectively through the guide bores in the pair of pivots associated with each tubular member. It is possible for the the bendable section constructed as above to improve the accuracy in alignment between the guide bores in the pivots associated with one of each pair of adjacent tubular members and the guide bores in the pivots associated with the other tubular member, because the pivots are beforehand determined in their respective positions.

Since, however, the respective end portions of the pair of pivots associated with each tubular member projects radially inwardly from the inner peripheral surface of the tubular member, the interior space of the tubular member is reduced correspondingly, thereby limiting or restricting the size of component parts accommodated in the tubular member so as to extend therethrough.

SUMMARY OF THE INVENTION

It is an object of the invention to provide an endoscope in which at least one pair of wire guide members can accurately be mounted to their respective positions on each of a plurality of tubular members forming a bendable section for an inserting portion, and in which it is possible to broadly and effectively utilize the interior space of each tubular member.

According to the invention, there is provided an endoscope comprising:

an operating body;

an inserting portion extending from the operating body, the inserting portion being provided with a bendable section at a forward end of the inserting portion remote from the operating body; and operating means for operating the bendable section to curve the same, the operating means including manipulating means mounted to the operating body for movement relative thereto, and at least one pair of manipulating wire means having their respective one ends operatively connected to the manipulating means, the other ends of the respective manipulating wire means being fixedly connected to substantially the vicinity of a forward end of the bendable section remote from the operating body, the bendable section including:

a plurality of tubular members arranged in facing relation to each other along an axis of the inserting portion;

connecting means arranged between each pair of adjacent tubular members for connecting them to each other for pivotal movement about an axis perpendicular to the axis of the inserting portion;

each of the tubular members being provided in its inner peripheral surface with a pair of recesses spaced 180 degrees from each other peripherally of the tubular member, each of the pair of recesses extending along an axis of the tubular member; and a plurality of pairs of wire guide members, each pair of wire guide members being mounted to a corresponding one of the tubular members, each pair of wire guide members being fixedly received respectively in the pair of recesses in a corresponding one of the tubular members, the pair of manipulating wire means extending respectively through the pair of wire guide members mounted to each of the tubular members.

DETAILED DESCRIPTION

The invention will be described below, by way of mere example, with reference to the accompanying drawings.

Figure 1:
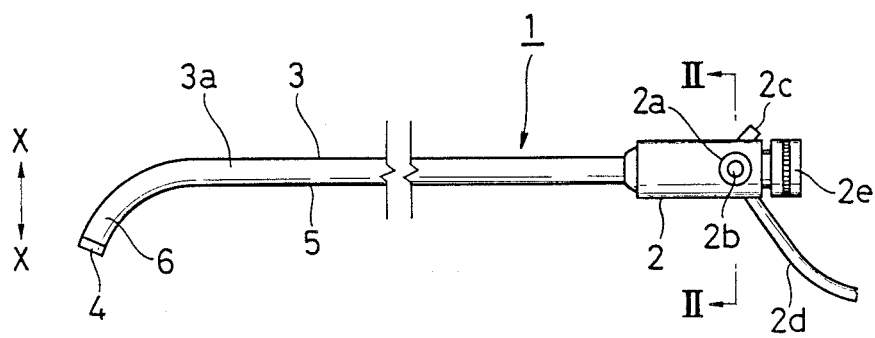
FIG. 1 is a side elevational view of the entirety of an endoscope comprising an inserting portion provided with an improved bendable section, according to an embodiment of the invention, with a part of the inserting portion omitted.

Referring first to FIG. 1, there is shown the entirety of an endoscope according to an embodiment of the invention, generally designated by the reference numeral 1. The endoscope 1 comprises an operating body 2, an elongated inserting portion 3 extending from a forward end face of the operating body 1, and a tip component 4 provided at a forward or distal end of the inserting portion 3.

A pair of first and second manipulating dials 2a and 2b are mounted to a side face of the operating body 2. A forceps insertion opening unit 2c is mounted to an upper surface of the operating body 2. A cable 2d extends from a lower surface of the operating body 2 and is connected to an illuminating light generating system (not shown). An eyepiece barrel 2e is connected to a end face of the operating body 2.

Figure 2:
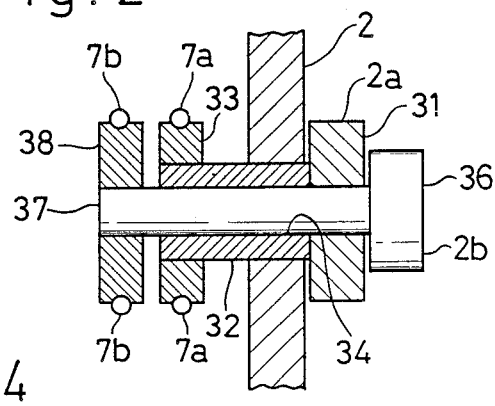
FIG. 2 is a fragmentary cross-sectional view of a pair of manipulating dials mounted to an operating body of the endoscope illustrated in FIG. 1.

As shown in FIG. 2, the first manipulating dial 2a is composed of a disc-like dial body 31 and a shaft section 32 projecting from one end face of the dial body 31. The shaft section 32 is mounted to the operating body 2 for angular movement relative thereto about an axis of the shaft section 32. The shaft section 32 has a forward end thereof which projects into the interior of the operating body 2. A pulley 33 is mounted on the forward end of the shaft section 32 for angular movement therewith about the axis of the shaft section 32. A central through bore 34 is formed through the dial body 31 and the shaft section 32. A pair of manipulating wires 7a and 7a, which will subsequently be described, have their respective rear ends which are fixedly connected to an outer peripheral surface of the pulley 33, at respective positions spaced 180 degrees from each other circumferentially of the pulley 33.

The second manipulating dial 2b is also composed of a disc-like dial body 36 and a shaft section 37 projecting from one end face of the dial body 36. The shaft section 37 extends through the through bore 34 in the first manipulating dial 2a in concentric relation to each other in such a manner that the shaft sections 32 and 37 of the respective manipulating dials 2a and 2b are movable relatively to each other angularly about the axis common to the shaft sections 32 and 37. The shaft section 37 of the second manipulating dial 2b has a forward end which projects from the forward end of the shaft section 32 of the first manipulating dial 2a. Another pulley 38 is mounted on the forward end of the shaft section 37 for angular movement therewith about the common axis of the shaft sections 32 and 37. A second pair of manipulating wires 7b and 7b, which will subsequently be described, have their respective rear ends which are fixedly connected to an outer peripheral surface of the pulley 38, at respective positions spaced 180 degrees from each other circumferentially of the pulley 38.

The inserting portion 3 is in whole covered with an outer envelope 3a (omitted from illustration except for FIG. 1) which is formed of resinous material having elasticity. The inserting portion 3 is composed of a flexible section 5 adjacent the operating body 2 and a bendable section 6 adjacent the tip component 4.

The tip component 4 is provided with a viewing window, an illuminating window and a forceps window (all not shown). The viewing window is optically connected to the eyepiece barrel 2e at the operating body 1 by an image transmitting system (not shown) which extends through the inserting portion 3. The illuminating window is optically connected to the cable 2d at the operating body 2 by an optical fiber (not shown) which extends through the inserting portion 3. The forceps window communicates with the forceps insertion opening 2c in the operating body 2 through a forceps channel (not shown) which extends through the inserting portion 3.

Figure 4:
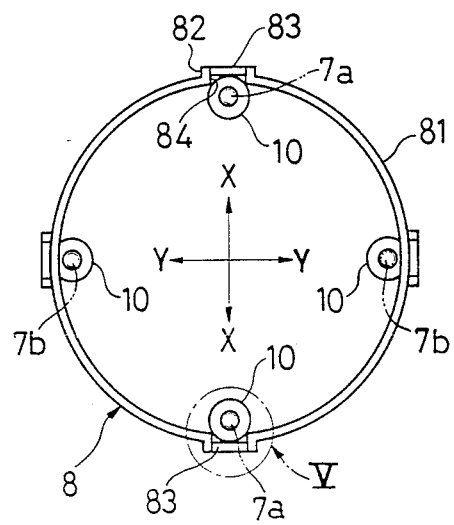
FIG. 4 is an enlarged front elevational view of the coaxially arranged tubular members as viewed from the arrow IV in FIG. 3.

Two pairs of manipulating wires 7a and 7a and 7b and 7b extend through the inserting portion 3. The first pair of manipulating wires 7a and 7a serve to curve the bendable section 6 in the arrowed direction X—X in FIG. 1, that is, in the arrowed direction X—X in FIG. 4. The first pair of manipulating wires 7a and 7a are arranged within the inserting portion 3 in such a manner as to be spaced from each other in the direction X—X. On the other hand, the second pair of manipulating wires 7b and 7b serve to curve the bendable section 6 in the arrowed direction Y—Y in FIG. 4 perpendicular to the direction X—X. The second manipulating wires 7b and 7b are arranged within the inserting portion 3 in such a manner as to be spaced from each other in the direction Y—Y. That is to say, the first pair of manipulating wires 7a and 7a are arranged within the inserting portion 3 in such a manner as to be spaced 180 degrees from each other circumferentially of the inserting portion 3. On the other hand, the second pair of manipulating wires 7b and 7b are arranged within the inserting portion 3 in such a manner as to be displaced 90 degrees circumferentially of the inserting portion 3, from the first pair of manipulating wires 7a and 7a. These four manipulating wires have their respective forward or distal ends which are fixedly connected to the tip component 4. The other or proximal ends of the respective first manipulating wires 7a and 7a are fixedly connected to the pulley 33 mounted to the shaft section 32 of the first manipulating dial 2a in the manner described above. Likewise, the proximal ends of the respective second manipulating wires 7b and 7b are fixedly connected to pulley 38 mounted to the shaft section 37 of the second manipulating dial 2b as described above. Accordingly, angular movement of the first manipulating dial 2a about the axis of the shaft section 32 thereof causes the bendable section 6 to be curved in the direction X—X, while angular movement of the second manipulating dial 2b about the axis of the shaft section 37 thereof causes the bendable section 6 to be curved in the direction Y—Y.

Four interlocked-flexible-metal-hoses (not shown) are accommodated in the flexible section 5 and extend therethrough. Each hose has one end thereof fixedly connected to the operating body 2, and the other end fixedly connected to a connection between the flexible section 5 and the bendable section 6. The aforesaid manipulating wires 7a, 7a, 7b and 7b extend respectively through the four hoses.

Figure 3:
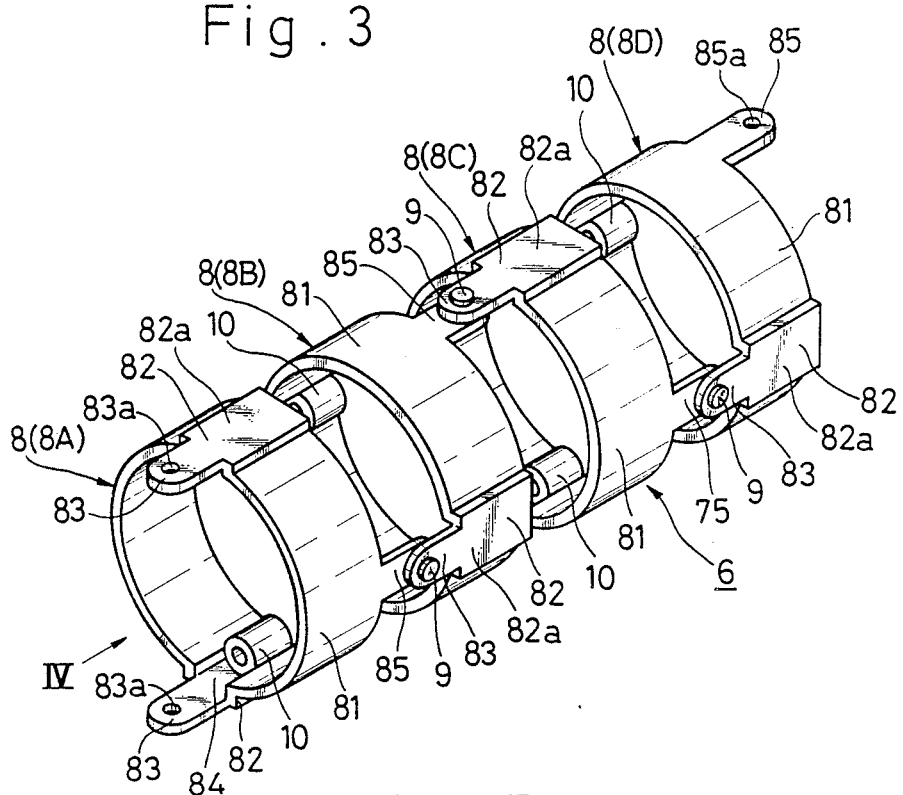
FIG. 3 is a fragmentary enlarged perspective view of the bendable section illustrated in FIG. 1, showing pivotal connection between each pair of adjacent tubular members.
Figure 5:
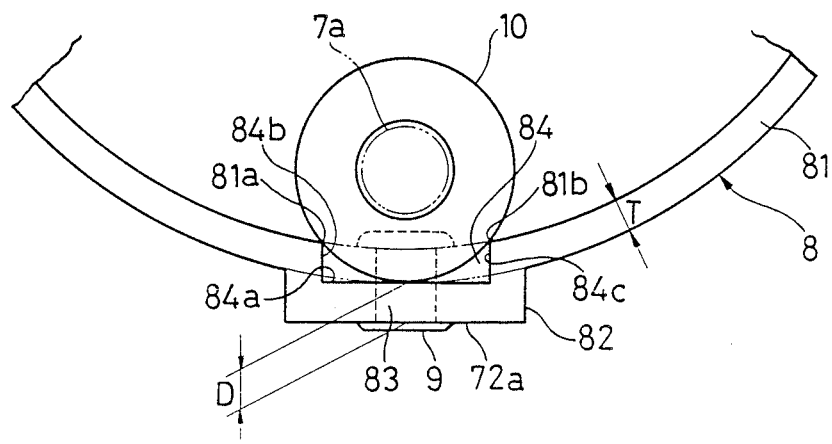
FIG. 5 is a fragmentary enlarged view of a portion encircled by V in FIG. 4.

As shown in FIG. 3, the bendable section 6 is composed of a plurality of tubular members 8 arranged in facing or coaxial relation to each other along the axis of the inserting portion 3. The tubular members 8 are formed to have the same configuration as each other. Each tubular member 8 has a cylindrical body 81. The cylindrical body 81 has a pair of wall portions thereof which are spaced 180 degrees from each other circumferentially of the cylindrical body 81, i.e., which are diametrically opposed to each other. The pair of wall portions of the cylindrical body 81 are so press-worked as to be formed respectively into a pair of projections 82 and 82. The pair of projections 82 and 82 project radially outwardly from an outer peripheral surface of the cylindrical body 81 so that a pair of recesses 84 and 84 are formed in an inner peripheral surface of the cylindrical body 81. Each projection 82 has a projecting size D (see FIG. 5) which is optional, but, in the illustrated embodiment, which is equal to or slightly larger than the wall thickness T of the cylindrical body 81 for the reasons to be described later. The projection 82 extends between the opposite axial ends of the cylindrical body 81. Each of the pair of projections 82 is integrally formed at its forward end with a tab 83 which projects from a bottom or outer wall section 82a of the projection 82 in parallel relation to the axis of the cylindrical body 81. The tab 83 is formed at its forward end with a connecting bore 83a having an axis thereof which extends perpendicularly to the axis of the cylindrical body 81.

The above-mentioned pair of recesses 84 and 84 formed in the inner peripheral surface of the cylindrical body 81 extend parallel to the axis thereof. Each recess 84 serves to determine the position and orientation of a corresponding one of wire guides 10 subsequently to be described. Accordingly, the recess 84 is optional in configuration and size, if the recess 84 can determine the position and orientation of the wire guide 10. In the illustrated embodiment, the recess 84 is rectangular in cross-sectional shape in a plane perpendicular to the axis of the cylindrical body 81. The recess 84 has a depth whose size is the same as the projecting size D.

The cylindrical body 81 is integrally provided with another pair of tabs 85 and 85 which are spaced 180 degrees from each other circumferentially of the cylindrical body 81. The pair of tabs 85 and 85 are arranged in relation displaced 90 degrees circumferentially of the cylindrical body 81, from the pair of tabs 83 and 83 at the axial forward end of the cylindrical body 81. Each tab 85 extends parallel to the axis of the cylindrical body 81, and has a forward end portion which is formed therein with a connecting bore 85a having an axis perpendicular to the axis of the cylindrical body 81.

A central one of adjacent three of the plurality of tubular members 8 constructed as above is pivotally connected to the left-and adjacent tubular member 8, and is pivotally connected to the right-hand adjacent tubular member 8 in relation displaced 90 degrees angularly about the axis of the inserting portion 3, relatively to the pivotal connection between the central tubular member 8 and the left-hand adjacent tubular member 8. Specifically, let it be supposed that the tubular member arranged at the left-hand end as viewed in FIG. 3 is designated by 8A, and the remaining tubular members arranged successively from the tubular member 8A to the right are designated respectively by 8B, 8C and 8D. Then, the tubular member 8B is arranged in relation circumferentially displaced 90 degrees relatively to the tubular member 8A. Further, the tubular members 8A and 8B are arranged in such a manner that the pair of tabs 83 and 83 at the axial forward end of the tubular member 8B face respectively the pair of tabs 85 and 85 at the axial rearward end of the the tubular member 8A. In this connection, since the radial projecting size D of each projection 82 is made substantially equal to the wall thickness T of the tubular member 81, the tabs 85 and 85 are located radially inwardly of the respective tabs 83 and 83 in such a manner that the radially outward surface of each tab 85 is substantially in contact with the radially inward surface of a corresponding one of the tabs 83. A pivot 9 such as a rivet or the like is rotatably inserted into the aligned bores 83a and 85a in the respective tabs 83 and 85 so that the tabs 83 and 85 are pivotally connected to each other. Thus, the tubular members 8A and 8B are connected to each other pivotally in the direction X—X in FIG. 3. Likewise, the tubular members 8B and 8C are pivotally connected to each other in such a manner that the tabs 85 and 85 at the axial rearward end of the tubular member 8B and the tabs 83 and 83 at the axial forward end of the tubular member 8C are pivotally connected to each other by the respective pivots 9 and 9. In this case, since the tabs 83 and 83 at the axial forward end of the tubular member 8C are displaced 90 degrees circumferentially of the tubular member 8C from the tabs 85 and 85 at the axial rearward end of the tubular member 8B, the tubular members 8C are connected to each other for pivotal movement in the direction Y—Y perpendicular to the direction X—X.

The pair of wire guides 10 and 10 are received respectively in the pair of recesses 84 and 84 of each tubular member 8. As clearly shown in FIG. 5, each wire guide 10 has a cylindrical outer peripheral surface which is in contact with a bottom surface 84a of a corresponding one of the recesses 84, and which is also in contact with a pair of intersections 81a and 81b between the inner peripheral surface of the cylindrical body 81 and a pair of opposed side surfaces 84b and 84c of the recess 84a. In this manner, the wire guide 10 is restricted in position circumferentially of the cylindrical body 81, and is so restricted that the wire guide 10 is oriented to have its axis parallel to the axis of the cylindrical body 81. The wire guide 10 is fixedly mounted to the cylindrical body 81 by bonding means such as brazing, welding or the like.

The manipulating wires 7a, 7a, 7b and 7b extend through their respectively associated groups of wire guides 10. In this connection, since each pair of adjacent tubular members 8 and 8 are displaced 90 degrees from each other, the wire guides 10 fixedly mounted to the tubular members 8A and 8C are arranged in relation displaced 90 degrees about the axis of the inserting portion 3 relatively to the wire guides 10 fixedly mounted to the tubular members 8B and 8D. Thus, the first pair of manipulating wires 7a and 7a for curving the bendable section 6 in the direction X—X extend respectively through the pair of wire guides 10 and 10 on the tubular member 8A and through the pair of wire guides 10 and 10 on the tubular member 8C. On the other hand, the second pair of manipulating wires 7b and 7b for curving the bendable section 6 in the direction Y—Y extend respectively through the pair of wire guides 10 and 10 on the tubular member 8B and through the pair of wire guides 10 and 10 on the tubular member 8D.

In the bendable section 6 constructed as above, it is ensured that the pair of wire guides 10 and 10 on the tubular member 8A and the pair of guides 10 and 10 on the tubular member 8C are aligned with each other, since each wire guide 10 is restricted in position and orientation by a corresponding one of the recesses 84. This is applicable to the two pairs of wire guides 10 and 10 on the respective tubular members 8B and 8D. Thus, it is avoided that excessive frictional resistance occurs between the manipulating wires 7a, 7a, 7b and 7b and the inner peripheral surfaces of the respective wire guides 10 when the manipulating wires are operated by the manipulating dials 2a and 2b. This enables the manipulating dials 2a and 2b to carry out bending or curving operation smoothly, and makes it possible to prevent the manipulating wires 7a, 7a, 7b and 7b from being torn up. Further, since the wire guide 10 is received in a corresponding one of the recesses 84, the size of the wire guide 10 projecting radially inwardly of the tubular member 8 can be reduced to the requisite minimum, thereby making it possible to broadly and effectively utilize the interior space of the tubular member 8.

It is to be understood that the invention is not limited to the above-described embodiment, but various changes and modifications can be made to the invention.

That is, although the endoscope has been described as having two pairs of manipulating wires 7a and 7a and 7b and 7b, only one of the two pairs of manipulating wires may be incorporated in the endoscope in such a manner that the bendable section 6 can be curved in any one of the directions X—X and Y—Y.

Moreover, although each recess 84 in the above embodiment has been described as having the rectangular cross-sectional shape, the recess 84 may be formed to have an arcuate cross-sectional shape along the outer peripheral surface of the wire guide 10.

Furthermore, each manipulating wire 7a, 8a has been described as having its forward end which is fixedly connected to the tip component 4. However, the forward end of the manipulating wire may be fixedly connected to one of the tubular members 8 which is located closest to the tip component 4.

In addition, it is to be understood that each tubular member 8 is not limited to the cylindrical shape shown in the figures, but may be elliptic in shape. Moreover, each pair of adjacent tubular members 8 and 8 may be different in configuration from each other.

What is claimed is:

1. An endoscope comprising:
   an operating body;
   an inserting portion extending from said operating body, said inserting portion being provided with a bendable section at a forward end of said inserting portion remote from said operating body; and
   operating means for operating said bendable section to curve the same, said operating means including manipulating means mounted to said operating body for movement relative thereto, and at least one pair of manipulating wire means having their respective one ends operatively connected to said manipulating means, the other ends of the respective manipulating wire means being fixedly connected to substantially the vicinity of a forward end of said bendable section remote from said operating body,
   said bendable section including:
   a plurality of tubular members arranged in facing relation to each other along an axis of said inserting portion;
   connecting means arranged between each pair of adjacent tubular members for connecting them to each other for pivotal movement about an axis perpendicular to the axis of said inserting portion;
   each of said tubular members being provided in its inner peripheral surface with a pair of recesses spaced 180 degrees from each other peripherally of the tubular member, each of the pair of recesses extending along an axis of the tubular member; and
   a plurality of pairs of wire guide members, each pair of wire guide members being mounted to a corresponding one of said tubular members, each pair of wire guide members being fixedly received respectively in the pair of recesses in a corresponding one of said tubular members, said pair of manipulating wire means extending respectively through the pair of wire guide members mounted to each of said tubular members.

2. An endoscope according to claim 1, wherein said connecting means comprises a first pair of tabs provided at an axial one end of each of said tubular members and extending from the axial one end of the tubular member axially thereof, the first pair of tabs being spaced 180 degrees from each other peripherally of the tubular member, and a second pair of tabs provided at the other axial end of the tubular member and extending from the other axial end of the tubular member axially thereof, the second pair of tabs being spaced 180 degrees from each other peripherally of the tubular member, and wherein the first pair of tabs on one of each pair of adjacent tubular members are pivotally connected respectively to the second pair of tabs on the other tubular member.

3. An endoscope according to claim 2, wherein the first pair of tabs provided at the axial one end of each of said tubular members are displaced 90 degrees peripherally of the tubular member from the second pair of tabs provided at the other axial end of the tubular member, and wherein said operating means includes a first pair of manipulating wire means for moving each tubular member pivotally about an axis extending between the first pair of tabs on the tubular member, and a second pair of manipulating wire means for moving the tubular member pivotally about an axis extending between the second pair of tabs on the tubular member.

4. An endoscope according to claim 3, wherein said first pair of manipulating wire means are arranged respectively at the same locations as the first pair of tabs on each tubular member, and said second pair of manipulating wire means are arranged respectively at the same locations as the second pair of tabs on the tubular member.

5. An endoscope according to claim 4, wherein said first pair of manipulating wire means extend respectively through the pair of wire guides on one of each pair of adjacent tubular members, and said second pair of manipulating wire means extend respectively through the pair of wire guides on the other tubular member.

6. An endoscope according to claim 1, wherein each of the pair of wire guide members mounted to each of said tubular members is cylindrical in shape, and each of the pair of recesses in the tubular member is rectangular in cross-sectional shape in a plane perpendicular to the axis of said inserting portion.

7. An endoscope according to claim 5, wherein each of the pair of wire guide members mounted to each of said tubular members is cylindrical in shape, and each of the pair of recesses in the tubular member is rectangular in cross-sectional shape in a plane perpendicular to the axis of said inserting portion.

8. An endoscope according to claim 7, wherein each of said tubular members has a pair of wall portions spaced 180 degrees from each other peripherally of the tubular member, the pair of wall portions projecting radially outwardly from an outer peripheral surface of the tubular member to form respectively the pair of recesses in the tubular member, each recess having a depth substantially equal to a wall thickness of the tubular member, the first pair of tabs associated with the tubular member being formed respectively at axial ends of the respective projecting wall portions, adjacent the axial one end of the tubular member.

* * * * *